United States Patent
Gammons et al.

(10) Patent No.: US 7,640,764 B2
(45) Date of Patent: Jan. 5, 2010

(54) PORTABLE COOLANT SYSTEM

(75) Inventors: Scott Gammons, Loudon, TN (US); Clifford E. Gammons, Loudon, TN (US)

(73) Assignee: Adroit Medical Systems, Inc., Loudon, TN (US)

( * ) Notice: Subject to any disclaimer, the term of this patent is extended or adjusted under 35 U.S.C. 154(b) by 291 days.

(21) Appl. No.: 11/530,136

(22) Filed: Sep. 8, 2006

(65) Prior Publication Data

US 2008/0060374 A1    Mar. 13, 2008

(51) Int. Cl.
*F25D 23/12* (2006.01)
*F25D 3/02* (2006.01)
*A61F 7/00* (2006.01)

(52) U.S. Cl. .......................... 62/259.3; 62/459; 607/104

(58) Field of Classification Search ................ 62/259.3, 62/459; 607/104
See application file for complete search history.

(56) References Cited

U.S. PATENT DOCUMENTS

| | | | |
|---|---|---|---|
| 4,844,072 A | 7/1989 | French et al. | |
| 5,245,221 A * | 9/1993 | Schmidt et al. | ............. 307/112 |
| 5,336,249 A | 8/1994 | Mahawili | |
| 5,476,489 A | 12/1995 | Koewler | |
| 5,486,207 A | 1/1996 | Mahawili | |
| 5,647,051 A | 7/1997 | Neer | |
| 5,806,335 A * | 9/1998 | Herbert et al. | ................ 62/434 |
| 5,865,841 A | 2/1999 | Kolen et al. | |
| 5,948,012 A | 9/1999 | Mahaffey et al. | |
| 6,086,609 A * | 7/2000 | Buckley | ..................... 607/104 |
| 6,176,869 B1 * | 1/2001 | Mason et al. | ............... 607/104 |
| 6,551,348 B1 | 4/2003 | Blalock et al. | |
| 6,962,600 B2 | 11/2005 | Lennox et al. | |

\* cited by examiner

*Primary Examiner*—William C Doerrler
(74) *Attorney, Agent, or Firm*—Knox Patents; Thomas A. Kulaga (57) ABSTRACT

A portable cooling system providing a controlled rate of cooling. The system includes a cool water device, a remote switching unit, and a thermal pad. The cool water device includes a coolant storage chamber separated from a pumping chamber by a baffle. The pumping chamber includes a pump and a discharge line with a flow restrictor for the fluid being returned from the thermal pad. In one embodiment, the remote switching unit actuates the portable cooling system and includes a timer feature for shutting down the system after a predetermined time. In another embodiment, the switching unit actuates a controller that sends a pulse stream to the pump to control the cooling water flow rate. The thermal pad includes fluid conduits that distribute the cooling water over the surface of the pad. In various embodiments, the thermal pad is a flat pad, a bonnet-shaped pad, and a cap-shaped pad.

19 Claims, 7 Drawing Sheets

PORTABLE COOLANT SYSTEM

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

1. Field of Invention

This invention pertains to a portable cooling system for applying a controlled rate of cooling to a person or object. More particularly, this invention pertains to portable device that includes a cool water supply, a remote, tethered switching unit, and a thermal pad through which cool water is circulated.

2. Description of the Related Art

It is advantageous to selectively apply a cooling treatment to patients. Hypothermic treatment is useful for emergency treatment of injured persons, particularly those who have experienced head trauma. Cooling the brain immediately after a trauma event often can protect the brain and/or prevent or reduce injury to the brain. But, not only the brain benefits from cooling treatment. A common first aid for sports injuries is to apply ice or cooling to the injured area.

Cooling treatment is also useful for providing comfort. Many menopausal women have found relief from hot flashes by using cooling treatment to quickly lower their body temperature during the onset of a hot flash.

Physicians have used various devices and techniques to cool the human body, including pharmacological cooling and various types of mechanically induced cooling. Mechanically induced cooling approaches generally fall into one of three categories: conductive, convective, or evaporative. While different implementations have been tried, many are limited by lack of practicality, difficulty of use, ineffectiveness, and/or excessive power consumption.

Conductive cooling therapy, that is a cooling treatment in which the heat transfer mechanism is conduction as opposed to radiation or convection, is known and has been used. Ice packs, although primitive, provide quick localized cooling. A disadvantage of ice packs is that it is difficult to control the rate of cooling. It is also known to circulate a cooled fluid through a thermal pad wrapped around an extremity of a person. The fluid is cooled using various techniques, including using a refrigerant to cool the fluid.

A variety of conductive cooling therapy devices are known. U.S. Pat. No. 4,844,072, titled "Liquid-circulating thermal therapy system," issued to French, et al., on Jul. 4, 1989, discloses a thermal therapy system 18 with a translucent reservoir 36 for indicating fluid level. A pump 96 mounted external to the reservoir 36 provides fluid to a thermal pad 22.

U.S. Pat. No. 5,336,249, issued to Mahawili on Aug. 9, 1994, titled "Portable body heating/cooling system and method of use," discloses a pump 22 located inside a reservoir 14 and operated by an external battery 24. The inlet to the pump 22 is protected by a grill 32 "to prevent ice from entering and interfering with operation of the pump 22 and motor 30." The supply and return tubes 18, 20, including their extensions 44, 48, have an internal diameter sized to minimize back pressure to the pump 22.

U.S. Pat. No. 5,476,489, issued to Koewler on Dec. 19, 1995, titled "Cold therapy system," discloses an open top bag 11 filled with ice and water that is carried by a cooler 2. The bag 11 includes tubing flanges 14, 15 that allow connections to the bag 11 from outside the cooler 2. A housing 3 is attached to the outside of the cooler 2 and contains a positive displacement pump 4 and pump control means 5. The pump 4 is driven by a variable speed motor.

U.S. Pat. No. 5,486,207, issued to Mahawili on Jan. 23, 1996, titled "Thermal pad for portable body heating/cooling system and method of use," discloses a portable reservoir 14 similar to that disclosed in U.S. Pat. No. 5,336,249. The supply and return tubes 18, 20, including their extensions 44, 48 have an internal diameter sized to minimize back pressure to the pump 22. The thermal pad 12 is formed from a single corrugated tube 50 following a serpentine path having a number of turns.

U.S. Pat. No. 5,647,051, issued to Neer on Jul. 8, 1997, titled "Cold therapy system with intermittent fluid pumping for temperature control," discloses a cooler 2 being a reservoir for water and ice and a housing 3 mounted on the exterior of the cooler 2. The housing 3 includes a pump 4 and pump control means 5. The pump 4 is a single-speed, positive displacement pump. A cover 34 protects the pump control means 5 from condensation or leakage from the pump. The return tube 29 contains a liquid crystal temperature indicator 47. The pump control means 5 includes a circuit generating a pulse stream having two components. One component operates at a high frequency, such as 2 kHz, with a 25% on duty cycle. The second component operates at a very low frequency having a period of approximately 9 seconds. The second component has three duty cycles of 50%, 25%, and 11%. The two component pulse stream is applied to the pump motor 20 to control the flow from the pump. The return line 29 includes an orifice 29a. "The purpose of orifice 19a is to control the descent of pressure in pad 7 during motor-off times."

U.S. Pat. No. 5,865,841, issued to Kolen, et al., on Feb. 2, 1999, titled "Cold therapy apparatus," discloses a reservoir 19 and an external pump/heat exchanger 13. "The pump/heat exchanger 13, under microprocessor control, continuously displaces a precise amount of re-circulation water with water from the constant temperature reservoir to precisely maintain the temperature of the circulation water exiting the pump/heat exchanger 13." "To ensure a uniform temperature distribution at the therapy site or sites, particularly when multiple bladders are used in series in post-bilateral surgery therapy, maximum flow rate and pressure through the circulation system is maintained."

U.S. Pat. No. 5,948,012, issued to Mahaffey, et al., on Sep. 7, 1999, titled "Cold therapy device," discloses a cold therapy unit 10 having two fluid loops. A first fluid loop includes a reservoir in an ice chest 14. The lid 16 to the ice chest 14 includes a manual control valve 17 and a first pump 18 that extends into the ice chest 14. The second fluid loop includes the electronic control unit 12 that includes an electronic valve 32, a second pump 34, a thermoelectric module 36, and a temperature probe 38. The first fluid loop charges the unit 10, after which the first fluid loop is isolated and the second fluid loop causes cool water to flow through a cold therapy pad 24. The second loop uses a thermoelectric module 36 to remove heat from the fluid loop. The first fluid loop is connected to the second fluid loop when the thermoelectric module 36 cannot maintain the cold temperature of the second fluid loop.

U.S. Pat. No. 6,551,348, issued to Blalock, et al., on Apr. 22, 2003, titled "Temperature controlled fluid therapy system," discloses a reservoir 12, a continuously variable pump 17 submersed in the reservoir 12, a temperature controlled fluid blanket 18, and temperature sensors 20, 22. The two temperature sensors 20, 22 determine a control signal that controls the operation (the speed) of the pump 17. A high frequency (greater than 20 kHz) pulse output from the pulse width modulator 130 correlates to the temperature measured by the sensors 20, 22 to control the average power delivered to the submersible pump 17 via a power source 42.

Known prior art devices provide operator controls on the thermal therapy device. Oftentimes, it is desirable for a patient to control the thermal therapy device, either to start/stop the device or to control the temperature of the therapy pad. Many times the patient has limited mobility, hence the need for the therapy device. For these patients, a remote control unit to operate the thermal therapy device is advantageous.

Certain thermal pads that use a temperature controlled liquid benefit from maintaining a minimum pressure within the conduits of the pad. Such minimum pressure is useful to prevent the conduits in the thermal pad from being crushed or otherwise restricted, thereby enabling fluid flow through the conduits.

Known prior art devices use complicated configurations to control the temperature of the fluid directed to the thermal pad. The complicated configurations increase the complexity and the cost of thermal therapy devices. It is advantageous to use a passive system to control the temperature of the fluid flowing through the thermal pad.

BRIEF SUMMARY OF THE INVENTION

According to one embodiment of the present invention, a portable cooling system for applying a controlled rate of cooling is provided. The system includes a self-contained cool water device that is attached to a remote switching unit and a thermal pad. The cool water device includes an insulated reservoir having a coolant storage chamber separated from a pumping chamber by a baffle. The coolant storage chamber is sized to receive a quantity of ice, either as a block or chunks, and store a quantity of water and melted ice. The baffle includes openings for water to flow between the coolant storage chamber and the pumping chamber. The pumping chamber includes a pump. The return line from the thermal pad has a discharge end inside the pumping chamber and near the intake of the pump.

In various embodiments, the cool water device includes a power supply for powering the pump, an input from a remote switching unit, inlet and outlet ports for connecting to a thermal pad, and one or more of a temperature sensor with a controller, a temperature indicator, and a water level indicator. In one embodiment, the cool water device is adapted to be powered from the standard power lines at 120Vac and from a dc power supply, such as a 12Vdc automotive electrical system. The circuitry handling the power source distribution to the pump and other components is contained in the cover, or lid, of the cool water device.

In one embodiment, a temperature sensor in the fluid line monitors the water temperature. The temperature information is input into a controller, which causes the pump output to pulsate to control the flow rate through the thermal pad. In another embodiment, the fluid line includes a temperature indicator for monitoring the fluid temperature to the thermal pad.

In certain applications, such as personal cooling at night, a remote switching unit plugs into the cool water device to control the operation of the portable cooling system. In one such embodiment, the system includes a timer that shuts down the system after a specified time elapses when the system is initiated with the remote switching unit.

The cool water device includes quick-release connectors for attaching a thermal pad. The outlet port is connected to the outlet of the pump. In one embodiment, a valve is in-line between the pump and the outlet port. The inlet port receives warmed fluid from the thermal pad and discharges a majority of the warmed fluid into the coolant storage chamber and a portion of the warm fluid is discharged into the pumping chamber. The inlet port is connected to a flow restrictor.

In various embodiments, the thermal pad includes flat pads and shaped pads, both of which include fluid channels that allow the cooled water from the outlet port to flow through the pad and exit to the inlet port in the cool water device. The shaped pads include a thermal pad that folds into a bonnet and a thermal pad that is preformed as a cap.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

An apparatus for a portable cooling system, generally shown as 10 in the figures, is disclosed. The apparatus is for providing thermal treatment to a person or object through a portable unit.

Figure 1:
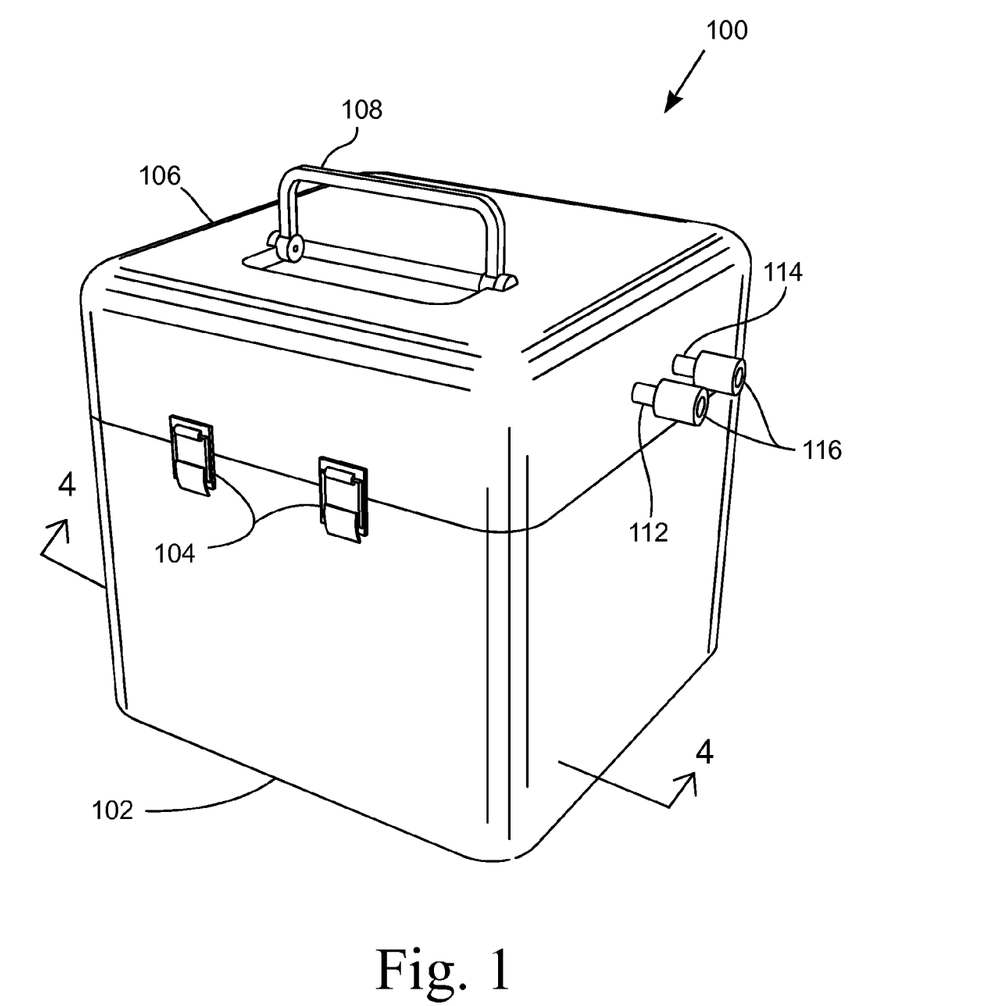
FIG. 1 is a perspective view of one embodiment of a cool water supply device.

FIG. 1 illustrates a perspective view of one embodiment of a cool water supply device 100. In the illustrated embodiment, the cool water device 100 resembles a portable ice chest and has some of the same features, such as a base, or reservoir, 102 and a lid, or cover, 106. The lid 106 includes a handle 108, and a pair of hasps 104 in the front secures the lid 106 to the base 102. The cool water device 102 is insulated and includes an outlet port 112 and an inlet port 114. The ports 112, 114 have connectors 116 for attaching the tubing for the thermal pad 200. In one embodiment, the connectors 116 are quick disconnect fittings.

Figure 2:
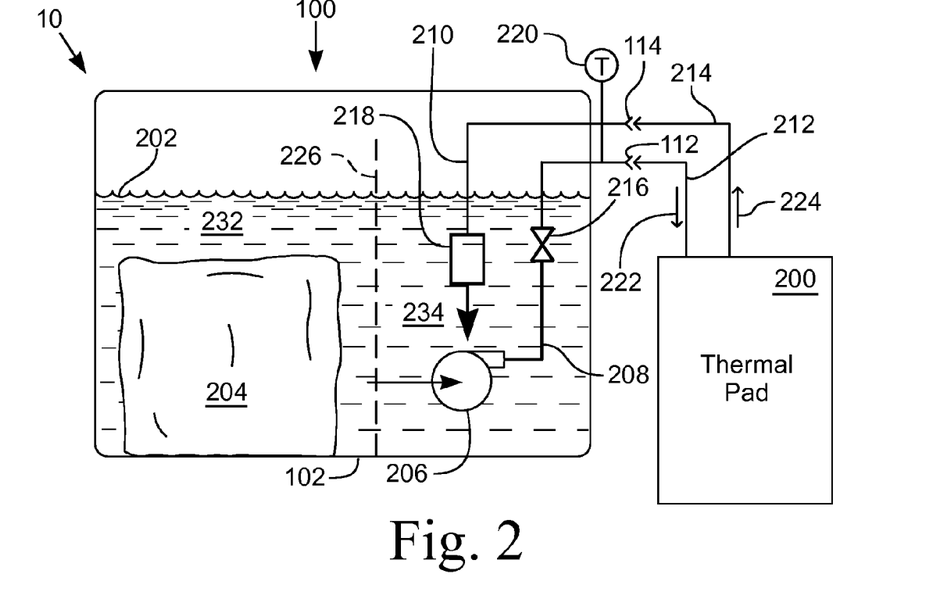
FIG. 2 is a flow diagram of one embodiment of the portable cooling system.

FIG. 2 illustrates a flow diagram of one embodiment of the portable cooling system 10. The system 10 includes the cool water device 100 and a thermal pad 200. The cool water device 100 includes the base 102, which is a reservoir with a coolant storage chamber 232 separated from a pumping chamber 234 by a baffle 226. The coolant storage chamber 232 holds ice 204, either in block or cube form. The cool water device 100 also contains a liquid fluid 202, such as water, that is in both chambers 232, 234. As the ice 204 melts, the quantity of fluid 202 increases until all the ice 204 melts.

In the illustrated embodiment, the pumping chamber 234 contains a pump 206 with an outlet connected to a valve 216 that is connected to the outlet port 112. In one embodiment, the pump 206 is a dc powered, single speed, submersible centrifugal, self-priming pump, such as commonly used for bilge pumps. In various embodiments, the valve 216 is either a flow control valve, a solenoid operated valve, or a diverter valve. In one embodiment, the valve 216 is a diverter, that is, the valve 216, diverts a portion of the flow from the pump 206 back to the pumping chamber 234, with the remaining fluid 202 flowing 222 to the thermal pad. The outlet tube 208 connected to the outlet port 112, in one embodiment, includes a temperature indicator 220 that provides indication of the temperature of the fluid 202 flowing 222 to the thermal pad 200. In one such embodiment, the temperature indicator 220 is a passive indicator, such as a strip with a temperature sensitive material indicating temperature. In another embodiment, the outlet tube 202 includes a temperature sensor 220 for measuring the temperature of the fluid 202.

The thermal pad 200 includes an inlet tube 212 and an outlet tube 224 that are connected to the outlet 112 and the inlet 114, respectively, of the cool water device 100. In various embodiments, the inlet tube 212 and the outlet tube 224 are attached to the thermal pad 200 by connectors or direct connections to the pad 200.

The inlet port 114 is connected to a discharge tube 210 that, in the illustrated embodiment, discharges in the vicinity of the intake to the pump 206. The discharge tube 210 from the inlet port 114 includes a flow restrictor 218. The flow restrictor 218 increases the back-pressure in the thermal pad 200 to ensure limit the flow through the pad 200 and to ensure that the pad 200 remains filled with fluid 202. In one embodiment, the flow restrictor 218 is a plug inserted in the end of the tube 210, and the plug has a small diameter opening or orifice. In another embodiment, the flow restrictor 218 is a flow control valve that is adjusted for the desired flow rate and/or back pressure in the thermal pad 200. That is, the valve 218 is variable in that it is adjustable between the open and closed positions to vary the flow through the valve 218. In still another embodiment, the flow restrictor 218 is a diverter, that is, the restrictor 218 allows only a portion of the return flow 224 to enter either chamber 232, 234 with the remainder of the flow 224 being diverted to the outlet port 112, where it becomes a portion of the flow 222 to the thermal pad 200, along with the fluid 202 from the pump 206.

The freezing point of water, and the melting point of ice, is 32 degrees Fahrenheit. For cooling therapy of the patient, a temperature of approximately 50 degrees Fahrenheit at the thermal pad 200 is considered optimum, with the range of temperature applied to patients being variable between 40 and 54 degrees Fahrenheit. In one embodiment, the portable cooling system 10 provides water 202 at 42 degrees Fahrenheit at the outlet port 112 for 180 minutes. By discharging a portion of the warmed water flow 224 near the intake of the pump 206, the outlet water flow 222 includes the cool water 202 and some of the water from the inlet flow 224. The warmed water from the inlet flow 224 combined with the cool water 202 maintains the water flow 222 to the thermal pad 200 at a temperature greater than 32 degrees.

In operation, cool water 202 flows into the suction side of the pump 206 and pushed through the valve 216. The valve 216 is operated to control the fluid flow 222 to the thermal pad 200. The warmed fluid from the thermal pad 200 flows 224 from the pad 200 to the discharge tube 210, where some of the warmed fluid enters the intake of the pump 206. The flow restrictor 218 controls the flow 222, 224 through the thermal pad 200 and ensures that there is sufficient back-pressure in the pad 200 to keep the pad 200 filled with fluid 202.

Figure 3:
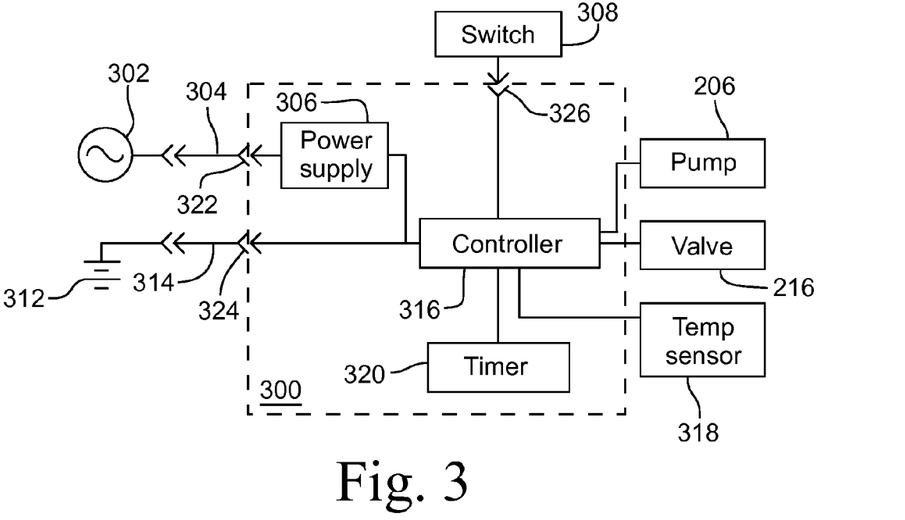
FIG. 3 is a block diagram of one embodiment of the portable cooling system.

FIG. 3 illustrates a block diagram of one embodiment of the portable cooling system 10. The system 10 includes a control module 300 that is configured to operate from either a standard ac power source 302 or a battery 312, such as an automotive battery or a battery pack. An ac power cable 304 connects the ac power source 302 to a power supply 306 that converts the ac power to a dc voltage that powers the remainder of the system 10. If it is desired to use dc power 312, a dc power cable 314 connects the battery 312 to the system 10. The ac power cable 304 plugs into an ac power connector 322 on the cool water storage device 100 and the dc power cable 314 plugs into a dc power connector 324 on the cool water storage device 100.

A remote switching unit 308 is a tethered device that connects to a switch connector 326 on the cool water storage device 100. In the illustrated embodiment, the remote switching unit 308 communicates with the controller 316. The control circuit 300 includes a timer 320 in communication with the controller 316. In various embodiments, the remote switching unit 308 includes one or more of a start switch, a stop switch, and a flow rate or speed switch.

In the illustrated embodiment, the controller 306 receives an input from a temperature sensor 220 and controls the pump 206 and the valve 216. In such an embodiment, the controller 306 is a device that controls a process, through one or more outputs, based on one or more inputs, such as a microcontroller, a programmable logic controller, an application specific integrated circuit (ASIC), an analog controller, or other device for implementing the control functions. In other words, the controller 316 is a device that interrupts power to the pump 206 in response to one or more input signals, such as from the remote switching unit 308.

In another embodiment, the portable cooling system 10 does not monitor the temperature of the fluid 202 or control the valve 216. In various such embodiments, the remote switching unit 308 operates the controller 316 or directly operates the pump 206. In one such embodiment, the remote switching unit 308 includes a timer 320 and the switching unit 308 provides a control signal for a predetermined time.

The ice 204 melts at a temperature just above 32 degrees Fahrenheit, but the optimum temperature at the thermal pad 200 is warmer than the cool water 202, which is near the melting temperature. The portable cooling system 10, in various embodiments, operates in different modes to control the temperature at the thermal pad 200 and to efficiently use the cooling power of the ice 204.

In one embodiment, the portable cooling system 10 operates for a pre-determined time period whenever the system 10 is turned on. In such an embodiment, the remote switching unit 308 includes a switch for turning on the pump 206. The controller 316 starts the pump 206 in response to the switching unit 308. The controller 316 also starts the timer 320, which provides the controller 316 with a stop signal after a pre-determined time period. The controller 316 stops the pump 206 when the controller 316 receives the stop signal from the timer 220. In such an embodiment, the controller 316 is a device that interrupts power to the pump 206 in response to a signal from the remote switching unit 308. In various such embodiments, the remote switching unit 308 includes a timer 320 such that the signal from the remote switching unit 308 is enabled for a specified period, thereby operating the pump 206 for such a period.

In another embodiment, the portable cooling system 10 operates with a selected duty cycle, that is, the pump 206 cycles at a selected rate to control the time that the water flows 222 to the thermal pad 200. In such an embodiment, the selected duty rate alternates at a low frequency, for example, the duty rate varies between having the pump 206 operate for ten seconds every minute to having the pump 206 operate for four minutes out of every five minutes. In such an embodiment, the remote switching unit 308 includes a switch for turning on the system 10 and another switch for controlling the duty rate. The controller 316 reads the remote switching unit 308 and the timer 320 to control the pump 206 to have the selected duty cycle.

In one such embodiment, the portable cooling system 10 operates with a high frequency duty cycle, that is, the pump 206 cycles at a selected rate to control the time that the water flows 222 to the thermal pad 200 and the frequency of the cycles is sufficiently high that the fluid flow 222 appears to be constant to the user of the thermal pad 200. That is, the high frequency duty cycle pulsing of the pump 206 does not result in a user detectable pulsing or throbbing at the pad 200. The controller 316 generates a pulse stream that powers the pump 206. In this embodiment, the pump 206 is a centrifugal pump and the motor of the pump 206 receives power in full voltage pulses that have a time width of between 1 millisecond and 1 second. The flow from the pump 206 ramps up when the pulse powers the pump 206 and the flow ramps down after the pulse stops. The centrifugal pump is contrasted to a positive displacement pump, which has a flow profile resembling a square wave.

In another such embodiment, the pump 206 is run continuously and the valve 216 is operated to meet the duty cycle requirements. In one such embodiment, the valve 216 is operated by the controller 316 to open and close with a specified frequency to control the flow 222 to the thermal pad 200. In such an embodiment, the selected duty rate alternates at a high frequency, for example, the valve 216 cycles several times a second. The remote switching unit 308 includes a switch for turning on the system 10 and another switch for controlling the duty rate. In another such embodiment, the valve 216 is a manual operated valve and the valve 216 is adjusted for the desired flow rate.

In another embodiment, the portable cooling system 10 operates at a specified temperature. In one embodiment, the flow rate 222 to the thermal pad 200 is adjusted such that the average temperature of the thermal pad 200 is maintained at a set point. As described above, the flow rate 222 is controlled by pulsing the pump motor 206, by pulsing the control valve 216, or by manually controlling the valve 216.

In another embodiment, the portable cooling system 10 provides contrast therapy in which a patient is exposed to consecutive changes of localized temperature therapy. In this embodiment, the controller 316, in combination with the timer 320, applies cool water flow 222 to the thermal pad 200 for intermittent periods. There have been studies that show that after four changes, the body adjusts to the intermittent temperature changes.

Figure 4:
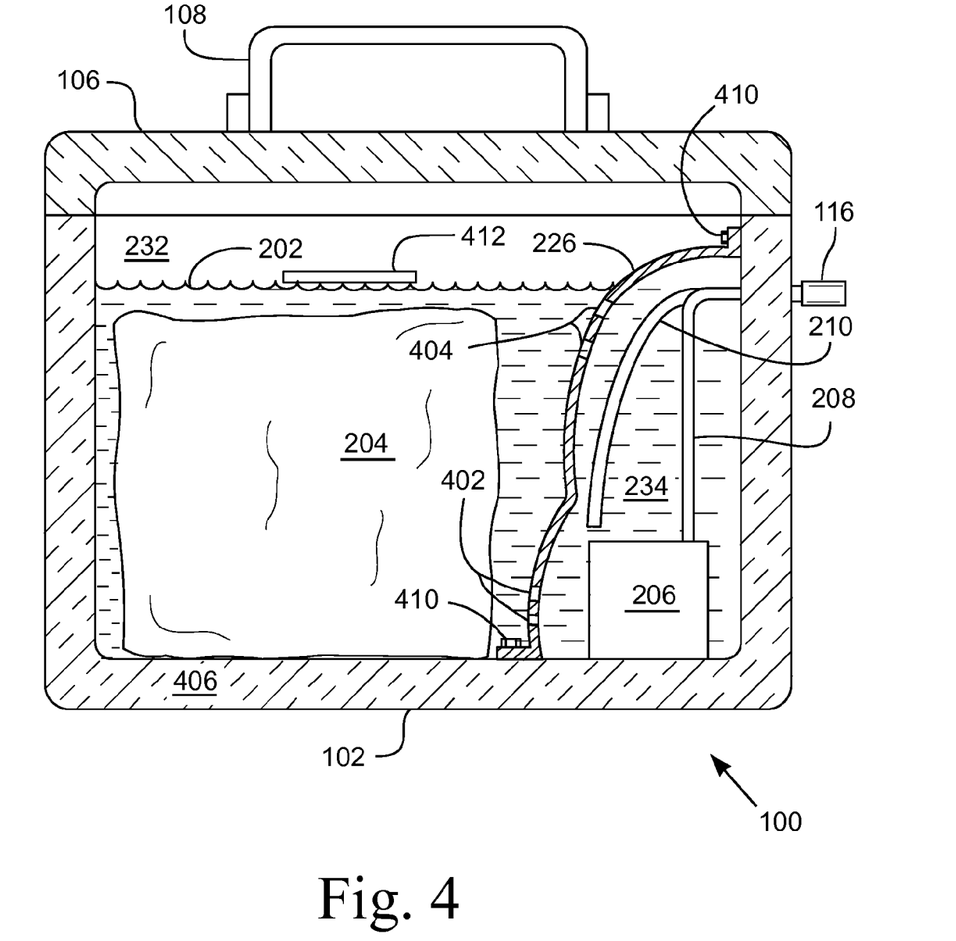
FIG. 4 is a cross-sectional view of one embodiment of the cool water supply device.
Figure 5:
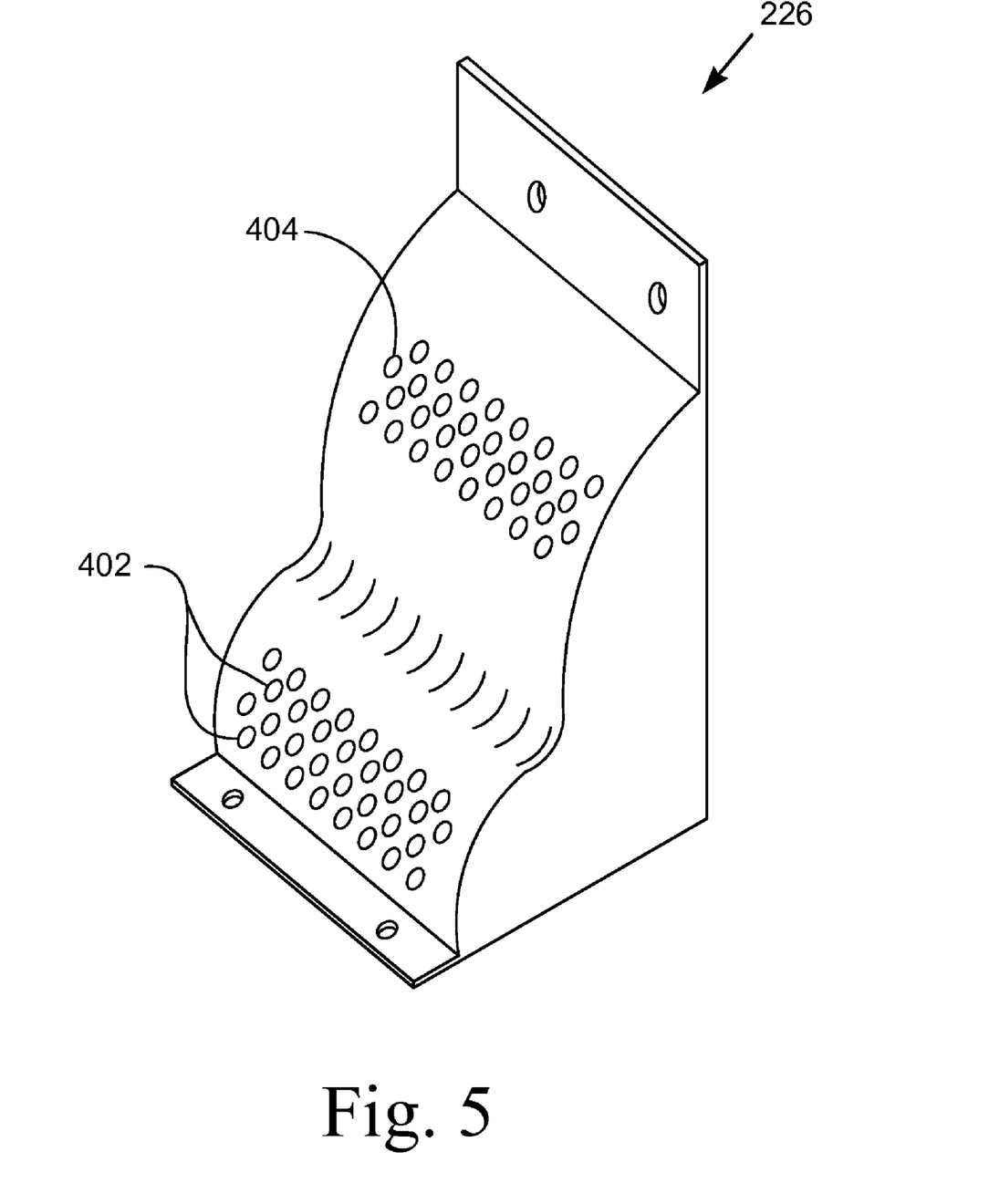
FIG. 5 is a perspective view of one embodiment of the baffle.

FIG. 4 illustrates a cross-sectional view of one embodiment of the cool water supply device 100. FIG. 5 illustrates a perspective view of one embodiment of the baffle 226. The cool water supply device 100 includes insulation 406 between its outside surface and the inside chambers 232, 234. The baffle 226 defines a pumping chamber 234 that is in fluid communication with the coolant storage chamber 232. The baffle 226 separates the coolant storage chamber 232 from the pumping chamber 234, and includes a group of lower passages 402 and a group of upper passages 404 that allow the fluid 202 to circulate between the coolant storage chamber 232 from the pumping chamber 234. In the illustrated embodiment, the passages 402, 404 are round openings allowing fluid to pass through the baffle 226. In other embodiments the passages 402, 404 are slots or other openings that allow the fluid 202 to move between the two chambers 232, 234.

The baffle 226 is attached to the inside surface of the base 102 with fasteners 410. The back and bottom of the baffle 226 generally conforms to the shape of the inside surface of the base 102. The lower portion of the baffle 226 is dimensioned and configured to enclose the pump 206 with the lower passages 402 adjacent the intake of the pump 206. The upper portion of the baffle 226 is dimensioned and configured to contain the tubing 208, 210 and, in various embodiments, the restrictor 218 and valve 216.

The embodiment illustrated in FIG. 4 shows the discharge tube 210 extending from the inlet port 114 to just above the pump 206. The outlet tube 208 extends from the pump 206 to the outlet port 112. In another embodiment, the inlet and outlet ports 114, 112 are positioned above the top of the baffle 226 with the discharge and outlet tubes 210, 208 penetrating the baffle 226. In one embodiment, the valve 216 is incorporated in the housing of the pump 206 and the flow restrictor 218 is incorporated in the discharge tube 210. In the illustrated embodiment, the inlet and outlet ports 112, 114 are at or below the water line of the fluid 202, thereby requiring a seal to prevent leakage. In another embodiment, the inlet and outlet ports 112, 114 are above the water line of the fluid 202.

The inside surface of the base 102 in the coolant storage chamber 232 has indicia 412 marking the low, high, and normal levels of the fluid 202. The indicia 412 is a passive fluid level indicator that is visible when the lid 106 in the open position.

Figure 6:
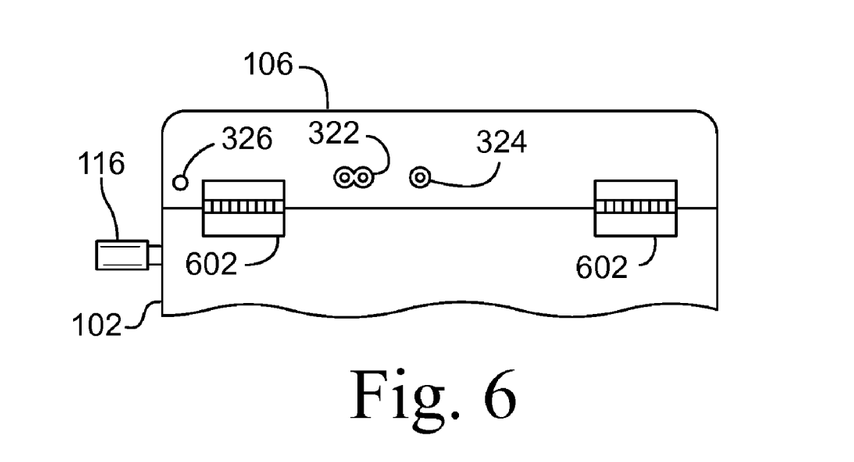
FIG. 6 is a partial rear view of one embodiment of the cool water supply device showing the electrical connections to the device.
Figure 7:
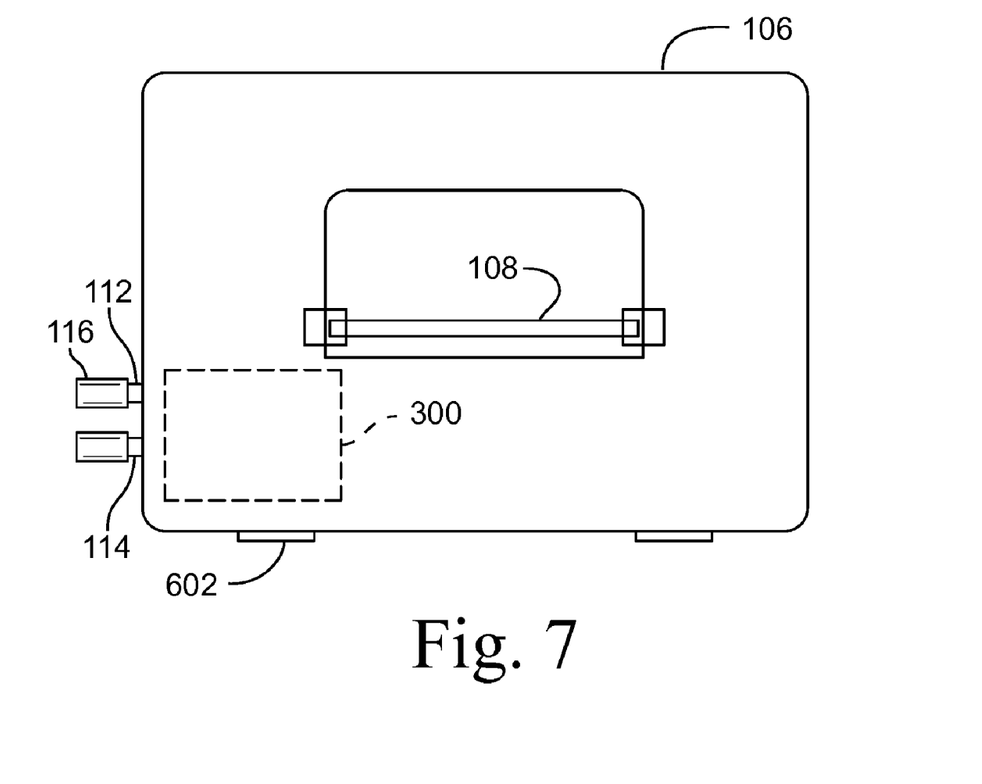
FIG. 7 is a top view of one embodiment of the cool water supply device showing the location of the power supply.

FIG. 6 illustrates a partial rear view of one embodiment of the cool water supply device 100 showing the electrical connections to the device 100. FIG. 7 illustrates a top view of one embodiment of the cool water supply device 100 showing the location of the power supply 306. The rear portion of lid 106 of the cool water supply device 100 is attached to the base with hinges 602. The control module 300 is inside the lid 106 with the external connections 322, 324, 326 on the outside of the lid 106 and the external connections to the pump 206 and valve 216 being inside the cool water supply device 100.

The remote switching unit 308 plugs into a connector 316 penetrating the lid 106. In one embodiment, the device 100 include one-half of a hook and loop fastening system that engages the other half of the hook and loop fastening system to secure the cable connecting the remote switching unit 308 to the connector 326 when the remote switching unit 308 is in a stored position. The ac power cable 304 and the dc power cable 314 each connects to a connector 322, 324 penetrating the lid 106. The power cables 304, 314 are secured in the stored position with a hook and loop fastening system.

Figure 8:
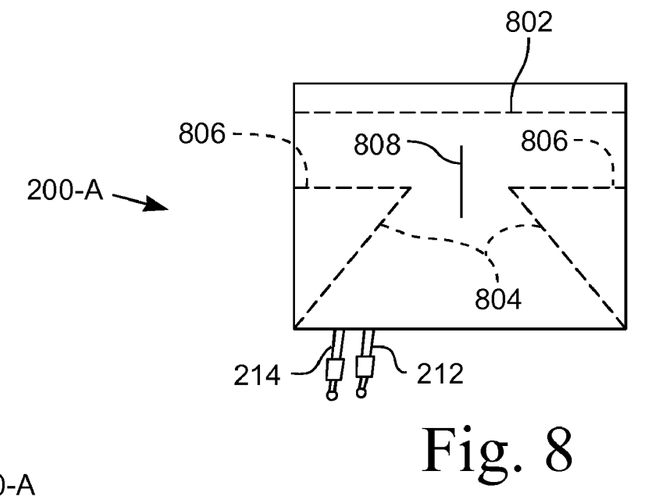
FIG. 8 is a plan view of one embodiment of a thermal pad in the open, flat position.
Figure 9:
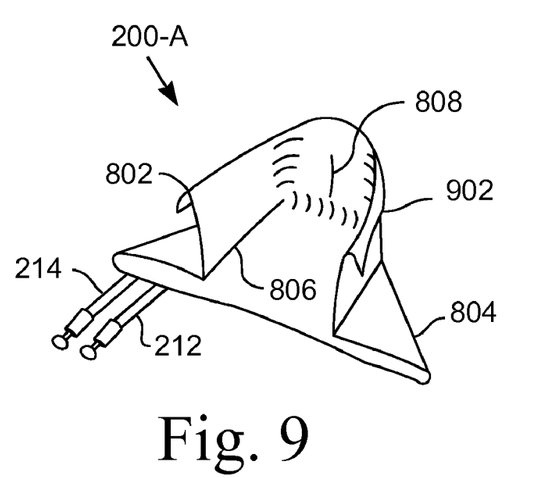
FIG. 9 is a perspective view of the thermal pad of FIG. 8 in the partially folded position.
Figure 10:
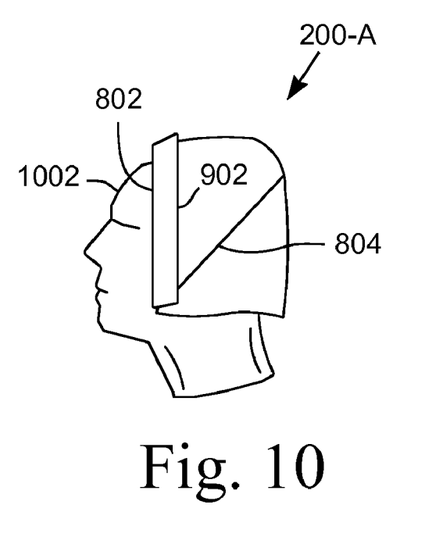
FIG. 10 is a side view of the embodiment of the thermal pad of FIGS. 8 & 9 as worn by a patient.

FIG. 8 illustrates a plan view of one embodiment of a thermal pad 200-A in the open, flat position. FIG. 9 illustrates a perspective view of the thermal pad 200-A of FIG. 8 in the partially folded position. FIG. 10 illustrates a side view of the embodiment of the thermal pad 200-A of FIGS. 8 & 9 as worn by a patient 1002. The illustrated embodiment of the thermal pad 200-A is a rectangular pad with internal cooling channels.

The pad 200-A has an access port 808 dimensioned and configured to provide access to the cranium of a person 1002 wearing the thermal pad 200-A.

The pad 200-A has a set of fold lines 802, 804, 806 that allow the rectangular pad 200-A to assume a snug bonnet shape with the brim 902 folded back at the brim fold line 802. The tips of the wings formed by folding at the diagonal lines 804 are tucked into the folded brim 902, thereby maintaining the thermal pad 200-A in the bonnet shape.

With the thermal pad 200-A folded to a bonnet-shape, the cranial access port 808 is positioned at the top of the crown of the person 1002. The cranial access port 808 allows access to the crown of the patient 1002 by medical personnel, such as during surgical procedures when it is desirable to provide cooling to the head of the patient 1002. In the illustrated embodiment, the access port 808 is a slit in the thermal pad 200-A. In other embodiments, the access port 808 is dimensioned and configured to allow access to the cranium of the patient 1002.

The illustrated embodiment shows the inlet and outlet tubes 212, 214 extending from the side of the bonnet-shaped thermal pad 200-A. In other embodiments, the tubes 212, 214 extend from the pad 200-A at a convenient location that still enables fluid flow within the thermal pad 200-A.

Figure 11:
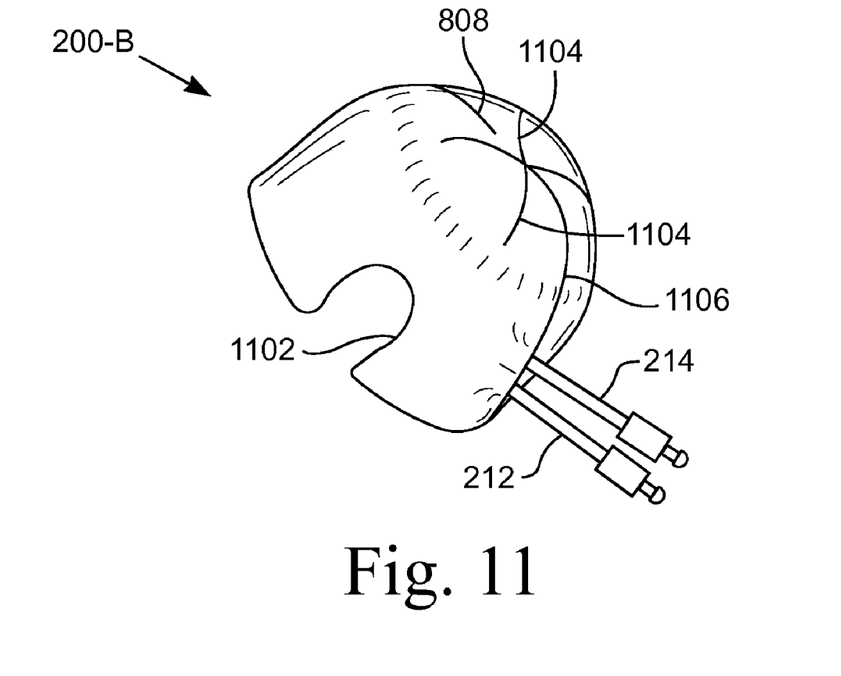
FIG. 11 is a perspective view of another embodiment of a thermal pad for cooling the head of a patient.
Figure 12:
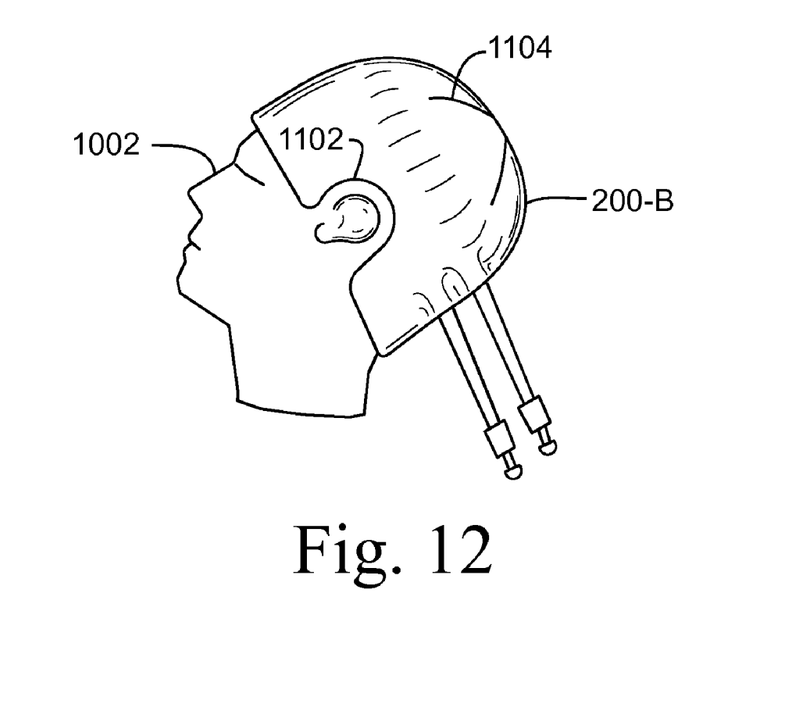
FIG. 12 is a side view of the embodiment of the thermal pad of FIG. 11 as worn by a patient.

FIG. 11 illustrates a perspective view of another embodiment of a thermal pad 200-B for cooling the head of a patient 1002. FIG. 12 illustrates a side view of the embodiment of the thermal pad 200-B of FIG. 11 as worn by a patient 1002. The illustrated embodiment of the thermal pad 200-B is generally cap-shaped. The thermal pad 200-B is formed from a planar pad that is joined at a side seam 1106 and with the crown of the pad 200-B formed by joining edges of the pad 200-B at the crown seams 1104. The sides of the thermal pad 200-B have a pair of cut-outs 1102 dimensioned and configured to fit around the ears of the patient 1002. The thermal pad 200-B has an access port 808 dimensioned and configured to provide access to the cranium of a person wearing the thermal pad 200-B.

The illustrated embodiment shows the inlet and outlet tubes 212, 214 extending from the edge of thermal pad 200-B at the side seam 1106. When the thermal pad 200-B is positioned on the head of the patient 1002, the tubes 212, 214 extend tangentially from the pad 200-B. In other embodiments, the tubes 212, 214 extend from the pad 200-B at a convenient location that still enables fluid flow within the thermal pad 200-A. In still another embodiment, the side seam 1106 is located at a position offset from the extreme rear of the thermal pad 200-B in the direction the tubes 212, 214 extend, thereby allowing the patient 1002 to lie face-up without having the tubes 212, 214 under the patient 1002 and applying pressure to the tubes 212, 214. In such an embodiment, the side seam 1106 is not centered between the ear cut-outs 1102.

The portable cooling system 10 includes various functions. The function of running the pump for a pre-determined time is implemented, in one embodiment, by the remote switching unit 308 and the timer 320 working in conjunction to start and stop the pump 206.

The function of elevating the temperature of the fluid 202 flowing 222 to the thermal pad 200 is implemented, in one embodiment, by the discharge end of the tubing, or conduit, 210 being configured to be proximal the intake of the pump 206. In another embodiment, the function of elevating the temperature is implemented by controlling the flow 222 of fluid 202 through the thermal pad.

The function of varying a flow rate 222, 224 through the thermal pad is implemented, in various embodiments, by controlling the duty cycle of the pump 206 and/or controlling the valve 216 as illustrated in FIG. 3.

From the foregoing description, it will be recognized by those skilled in the art that a portable cooling system 10 including a cool water device 100, a remote switching unit 308, and a thermal pad 200 has been provided. The cool water storage device 100 has two chambers 232, 234, one chamber 232 for the ice-fluid mixture 204, 202 and the other chamber 234 for containing the pump and allowing mixing of the warmer return flow 224 with the fluid 202 in the chamber 234. The remote switching unit 308 is a tethered device that allows an operator to control the portable cooling system 10. The thermal pad 200 is dimensioned and configured to meet the requirements of the particular therapy to be applied to the patient 1002.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for providing a controlled rate of cooling, said apparatus comprising:
   a cool water supply device having a reservoir and a cover, said reservoir of said cool water device having a first chamber and a second chamber, said first and second chamber each having a bottom proximate a bottom of said reservoir, said first chamber configured to receive a quantity of ice, said reservoir configured to receive a quantity of a liquid, said cool water supply device having an inlet port and an outlet port;
   a baffle defining said second chamber, said first chamber in fluid communication with said second chamber through a plurality of passages in said baffle;
   a pump in said second chamber, said pump having an intake and a discharge, said discharge of said pump in fluid communication with said outlet port of said cool water supply device;
   a switching unit operatively connected to said pump to cause said pump to start, said switching unit being operable at a distance from said cool water supply device;
   a thermal pad in fluid communication with said inlet port and said outlet port of said reservoir;
   a conduit having a first end connected to said inlet port of said reservoir; said conduit having a second end positioned in said second chamber, said conduit configured to discharge said fluid from said thermal pad proximal said intake of said pump; and
   a flow restrictor in said conduit, said flow restrictor dimensioned and configured to maintain a selected back pressure in said thermal pad;
   whereby said liquid is forced by said pump through said thermal pad, and a portion of said liquid returning to said cool water supply device after passing through said thermal pad flows directly into said intake of said pump.

2. The apparatus of claim 1 wherein said pump stops a pre-selected period of time after said pump is started by said switching unit.

3. The apparatus of claim 1 wherein said flow restrictor is selected from a group including an orifice and a valve, said orifice having a through-opening smaller in diameter than an inside diameter of said conduit, said valve being variable between an open position and a closed position, said valve being adjustable to a selected flow rate.

4. The apparatus of claim 1 further including a control module configured to control said pump, said control module dimensioned and configured to be contained within said cover of said cool water supply device, said switching unit connected to said control module.

5. The apparatus of claim 4 further including a control valve in a fluid loop between said discharge of said pump and said second end of said conduit, said control valve cycled between an open position and a closed position at a selected rate to limit said liquid flowing through said thermal pad.

6. The apparatus of claim 1 wherein said thermal pad is configured to fit on a head of a patient, said thermal pad having a bonnet-shape with a folded brim and a pair of folded side-wings, said thermal pad having an access port dimensioned and configured to provide access to a cranium of said patient.

7. The apparatus of claim 1 further including a means for varying a flow rate through said thermal pad.

8. An apparatus for providing a controlled rate of cooling, said apparatus comprising:
- a cool water supply device having a reservoir and a cover, said reservoir of said cool water device having a first chamber and a second chamber, said first chamber configured to receive a quantity of ice, said reservoir configured to receive a quantity of a liquid, said cool water supply device having an inlet port and an outlet port;
- a baffle dividing a bottom portion of said reservoir and defining a barrier between said first chamber and said second chamber, said first chamber in fluid communication with said second chamber through a plurality of passages in said baffle;
- a pump in said second chamber, said pump having an intake and a discharge, said intake positioned proximate a bottom of said reservoir in said second chamber, said discharge of said pump in fluid communication with said outlet port;
- a thermal pad in fluid communication with said inlet port and said outlet port of said reservoir; and
- a conduit having a first end connected to said inlet port of said reservoir; said conduit having a second end positioned in said second chamber, said conduit configured to discharge said fluid from said thermal pad proximate said intake of said pump;
- whereby said liquid is forced by said pump through said thermal pad, and a portion of said liquid returning to said cool water supply device after passing through said thermal pad flows directly into said intake of said pump such that a temperature of said liquid forced through said pump is greater than a temperature of said liquid in said first chamber.

9. The apparatus of claim 8 further including a switching unit operatively connected to said pump to cause said pump to start, said switching unit being operable at a distance from said cool water supply device.

10. The apparatus of claim 9 wherein said pump stops a pre-determined period of time after said pump is started by said switching unit.

11. The apparatus of claim 8 further including a flow restrictor in said conduit, said flow restrictor dimensioned and configured to maintain a predetermined back pressure in said thermal pad.

12. The apparatus of claim 11 wherein said flow restrictor is selected from a group including an orifice and a valve, said orifice having a through-opening smaller in diameter than an inside diameter of said conduit, said valve being variable between an open position and a closed position, said valve being adjustable to a selected flow rate.

13. The apparatus of claim 8 further including a control module configured to control said pump, said control module dimensioned and configured to be contained within said cover of said cool water supply device.

14. The apparatus of claim 13 further including a control valve in a fluid loop between said discharge of said pump and said second end of said conduit, said control valve operatively connected to said control module, said control valve cycled between an open position and a closed position at a selected rate to limit said liquid flowing through said thermal pad.

15. The apparatus of claim 8 wherein said thermal pad is configured to fit on a head of a patient, said thermal pad having a bonnet-shape with a folded brim and a pair of folded side-wings, said thermal pad having an access port dimensioned and configured to provide access to a cranium of said patient.

16. An apparatus for providing a controlled rate of cooling, said apparatus comprising:
- a cool water supply device having a reservoir and a cover, said reservoir of said cool water device having a first chamber and a second chamber, said cover closing a top of said first chamber, said first chamber configured to receive a quantity of ice through the top of the first chamber when said cover is open, said reservoir configured to receive a quantity of a liquid, said cool water supply device having an inlet port and an outlet port;
- a baffle defining said second chamber, said first chamber in fluid communication with said second chamber through a plurality of passages,
- a pump in said second chamber, said pump having an intake and a discharge, said intake positioned proximate a bottom of said reservoir in said second chamber, said discharge of said pump in fluid communication with said outlet port;
- a switching unit operatively connected to said pump to cause said pump to start, said switching unit being operable at a distance from said cool water supply device, said pump stopping a pre-selected period of time after said pump is started;
- a control module configured to control said pump, said control module dimensioned and configured to be contained within said cover of said cool water supply device, said switching unit in communication with said control module;
- a thermal pad in fluid communication with said inlet port and said outlet port of said reservoir; and
- a conduit having a first end connected to said inlet port of said reservoir; said conduit having a second end positioned proximal said intake of said pump;
- whereby said liquid is forced by said pump through said thermal pad for said pre-selected period.

17. The apparatus of claim 16 further including a means for varying a flow rate through said thermal pad.

18. The apparatus of claim 16 further including a flow restrictor in said conduit, said flow restrictor dimensioned and configured to maintain a predetermined back pressure in said thermal pad, said flow restrictor selected from a group including an orifice and a valve, said orifice having a through-opening smaller in diameter than an inside diameter of said conduit, said valve being variable between an open position and a closed position, said valve being adjustable to a selected flow rate.

19. The apparatus of claim 16 further including a control valve in a fluid loop between said discharge of said pump and said second end of said conduit, said control valve operatively connected to said control module, said control valve cycled between an open position and a closed position at a selected rate to limit said liquid flowing through said thermal pad.

* * * * *